(12) United States Patent
Spain et al.

(10) Patent No.: US 6,797,497 B1
(45) Date of Patent: Sep. 28, 2004

(54) BIOLOGICAL PROCESS FOR THE PRODUCTION OF ORTHO-AMINOPHENOLS FROM NITROAROMATIC COMPOUNDS USING MUTASE

(75) Inventors: Jim C. Spain, Panama City, FL (US); Lloyd J. Nadeau, Panama City, FL (US); Zhongqi He, Glenburn, ME (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 154 days.

(21) Appl. No.: 10/076,383

(22) Filed: Feb. 19, 2002

Related U.S. Application Data

(60) Provisional application No. 60/269,003, filed on Feb. 16, 2001.

(51) Int. Cl.$^7$ ................................................. C12P 13/00
(52) U.S. Cl. .................... 435/128; 435/170; 435/253.3; 435/193
(58) Field of Search ................................ 435/128, 170, 435/253.3, 874, 193

(56) References Cited

PUBLICATIONS

J. K. Davis et al, Sequence Analysis and Initial Characterization of Two Isozymes of Hydroxylaminobenzene Mutase from *Pseudomonas pseudoalcaligenes* JS45, Appl. Environ. Microbiol., vol. 66, No. 7, 2965–2971, 2000.*

Nishino and Spain, Degradation of nitrobenzene by a *Pseudomonas pseudoalcaligens*, Appl. Environ. Microbiol., 59: 2520–2525 (1993).*

Somerville, Nishino, and Spain, Purification and characterization of nitrobenzene nitroreductase from *Pseudomonas pseudoalcaligens* JS45, J. Bacteriol., 177: 3837–3842 (1995).*

He, Nadeau and Spain, Characterization of hydroxylaminobenzene mutase from pNBZ139 derived from *Pseudomonas pseudoalcaligenes* JS45: a highly–associated sodium–dodecyl–sulfate–stable enzyme catalyzes an intramolecular transfer of hydroxyl groups, Eur. J. Bioch., 267: 1110–1116 (2000).*

Furniss, Hannaford, Smith and Tatchell, Vogel's Textbook of Practical Organic Chemistry, John Wiley & Sons, New York, 1989.*

Nadeau et al, Production of 2–amino–5–phenoxyphenol from 4–nitrobiphenyl ether using nitrobenzene nitroreductase and hydroxylaminbenzene mutase from *Pseudomonas pseudoalcaligenes* JS45, J. Industrial Microbiology & Biotechnology (2000), 24, 301–305.*

* cited by examiner

*Primary Examiner*—Irene Marx
(74) *Attorney, Agent, or Firm*—Charles E. Bricker; Thomas L. Kundert

(57) ABSTRACT

A process for the production of ortho-aminophenols from nitroarenes using a biocatalyst consisting of pure enzymes, partially purified enzymes, cell lysate, intact cells, or a metal reaction linked with a subsequent enzymatic reaction. The biocatalyst is an enzyme system that makes use of a nitroreductase enzyme that initially reduces the nitroarene to the hydroxylaminoarene and a mutase enzyme that converts the hydroxylaminoarene to an ortho-aminophenol. The biocatalyst can also consist of a coupled, two-step metal and enzyme reaction in which the metal, such as zinc, catalyzes the transformation of the nitroarene to the hydroxylaminoarene and the mutase then catalyzes the transformation of hydroxylaminoarene to the corresponding ortho-aminophenol.

2 Claims, 3 Drawing Sheets

Transformation of 4-nitrobiphenyl ether (■) via 4-hydroxylaminobiphenyl ether (●) to 2-amino-5-phenoxyphenol (♦).

Transformation of nitrobenzene (■) to 2-aminophenol (●).

Transformation of 2-nitrotoluene (■) to 2-amino-3-methylphenol (●)

Transformation of 4-nitrotoluene (■) to 2-amino-4-methyphenol (●).

Transformation of 1-nitronaphthalene (■) to 1-amino-2-naphthol(●)

Whole-cell transformation of 4-nitrobiphenyl ether (■) to 2-amino-5-phenoxyphenol (♦).

BIOLOGICAL PROCESS FOR THE PRODUCTION OF ORTHO-AMINOPHENOLS FROM NITROAROMATIC COMPOUNDS USING MUTASE

CROSS REFERENCE TO RELATED APPLICATION

This application claims priority of the filing date of Provisional Application serial No. 60/269,003, filed Feb. 16, 2001, the entire contents of which are incorporated herein by reference.

RIGHTS OF THE GOVERNMENT

The invention described herein may be manufactured and used by or for the Government of the United States for all governmental purposes without the payment of any royalty.

BACKGROUND OF THE INVENTION

The present invention relates to biological production of ortho-aminophenols from nitroaromatic compounds Nitroaromatic compounds are used in the production of dyes, plastics, high explosives, pharmaceuticals and pesticides. Nitrobenzene (NB) alone is discharged to the environment at a rate of tens of millions of pounds annually. In addition, nitrated polycyclic aromatic hydrocarbons are formed during a variety of combustion processes and are common environmental contaminants. Considerable effort has been expended to clean environmentally contaminated sites at or near explosives production facilities. Reduction of the nitro group is a common first step in the biotransformation of nitroaromatic compounds, whether leading to mineralization of the compound or to the accumulation of dead-end products, many of which are cytotoxic and/or mutagenic.

Several biodegradation studies have shown that *Pseudomonas pseudoalcaligenes* strain JS45 and a variety of other isolates grow on nitrobenzene as the sole source of carbon and nitrogen. The reaction proceeds via two initial intermediates, hydroxylaminobenzene and ortho-aminophenol. The enzymes involved in catalyzing the initial steps are a nitroreductase and a hydroxylaminobenzene mutase. On first inspection the reaction seems similar to the nonenzymatic Bamberger rearrangement. The mechanism of the reactions and the stereochemistry of the products are distinctively different, however. The nitroreductase from strain JS45 has been purified and characterized as a flavoprotein requiring NADPH as an electron donor. Two genes expressing hydroxylaminobenzene mutase activity, have been cloned from strain JS45 and expressed in *E. coli* (J. K. Davis et al, Appl. Environ. Microbiol., Vol. 66, No. 7, 2965–2971, 2000), and one mutase enzyme, HabB (Z. He et al, Eur. J. Biochem., Vol. 267, 1110–1116, 2000), has been partially purified. JS45 was deposited in the American Type Culture Collection Patent Deposit in January, 2002, Patent Deposit Designation PTA-3972. Other reports have demonstrated that bacteria, such as *Clostridium acetobutylicum, Raistonia eutrophus* JMP134, *Pseudomonas putida, Pseudomonas putida* HS12, strain LW1 of the Comamonadaceae family, and *Pseudomonas putida* 2NP8, synthesize nitroreductases and hydroxylaminoarene mutases that transform a wide range of nitroaromatic compounds to the corresponding aminophenols. The metabolic degradation processes in the above strains are comparable to that described for *P. pseudoalcaligenes* strain JS45. It should be noted that these studies have been directed to biodegradation, i.e, the breakdown of organic compounds into more cell biomass and less complex compounds, and ultimately to water, and either carbon dioxide or methane. The above-described intermediates have been proposed or noted as intermediates in the biodegradation process(es), and have not been seen as end-products per se.

Orthoaminophenols are important intermediates in the synthesis of common azo dyes and phenoxazinones. They are a key feedstock for the synthesis of polybenzoxazole polymers. The substituents carried by the ortho-aminophenol confer to the benzoxazole products properties that are useful in electronic, opto-electronic, pharmaceutical, medical, military and biosynthetic applications. Commercially useful substituted ortho-aminophenols are difficult to chemically synthesize.

The common route for commercial synthesis of aminophenols occurs in two steps, nitration of phenol followed by reduction of the nitro-group with a metal to make the amine. The influence of the hydroxyl moiety varies with each substrate. For example, for phenol the substitution is directed preferentially to the ortho position, but for naphthalene the para position is more readily attacked. In either case, yields are very low for mononitration of phenols and conditions needed are extreme.

Accordingly, it is an object of the present invention to provide a process for the biological production of aminophenols.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there is provided a process for the production of ortho-aminophenols from nitroarenes using a biocatalyst consisting of pure enzymes, partially purified enzymes, cell lysate, intact cells, or a metal reaction linked with a subsequent enzymatic reaction. The biocatalyst is an enzyme system that makes use of a nitroreductase enzyme that initially reduces the nitroarene to the hydroxylaminoarene and a mutase enzyme that converts the hydroxylaminoarene to an ortho-aminophenol. As noted previously, a variety of bacteria produce these enzymes and can be used as the source(s) for the enzymes. The biocatalyst can also consist of a coupled, two-step metal and enzyme reaction in which the metal, such as zinc, catalyzes the transformation of the nitroarene to the hydroxylaminoarene and the mutase then catalyzes the transformation of hydroxylaminoarene to the corresponding ortho-aminophenol.

The reaction scheme can be represented as follows:

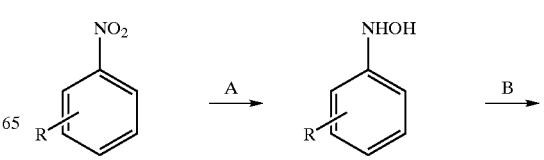

-continued

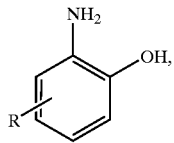

wherein R is selected from the group consisting of —H, —OH, —COOH, —$C_nH_{2n+1}$, —$C_6H_5$, —X, —$CX_3$, —CHO, —$OC_nH_{2n+1}$, and —O—$C_6H_5$, wherein n ranges from 1 to 6, X is F, Cl, Br or I, A represents, but is not limited to, a nitroreductase or a metal such as zinc, and B represents the mutase enzyme.

DETAILED DESCRIPTION OF THE INVENTION

Figure 1:
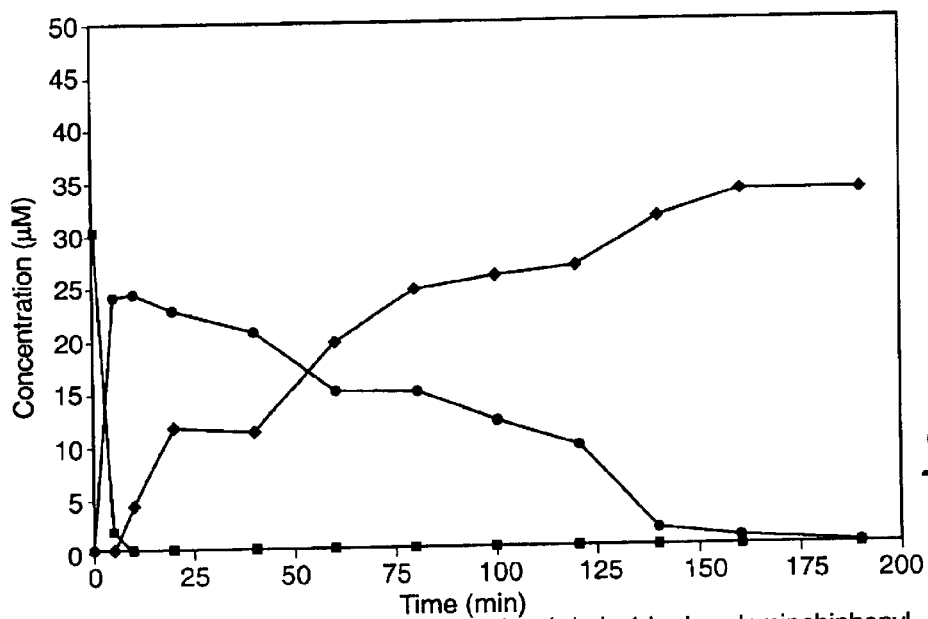
FIG. 1 illustrates the transformation of 4-nitrobiphenyl ether via 4-hydroxylaminobiphenyl ether to 2-amino-5-phenoxyphenol.
Figure 2:
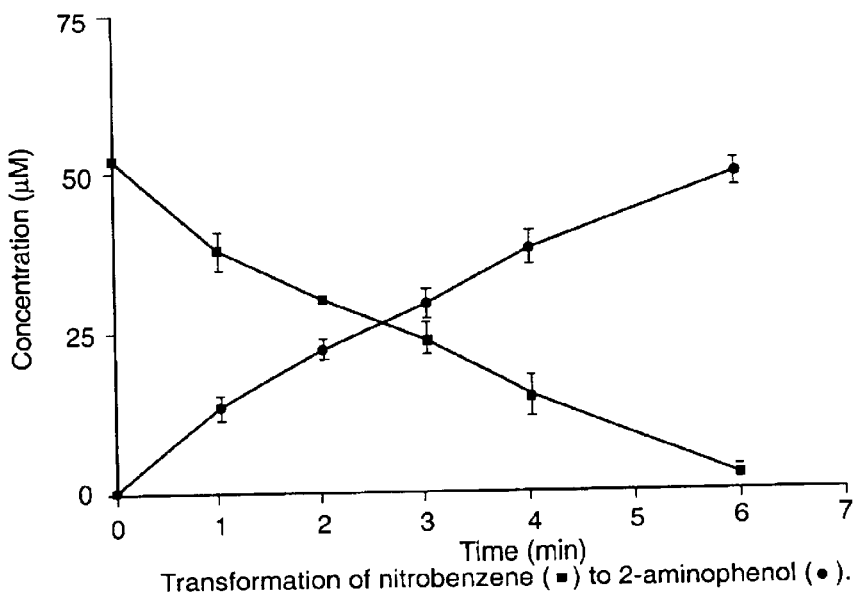
FIG. 2 illustrates the transformation of nitrobenzene to 2-aminophenol.
Figure 3:
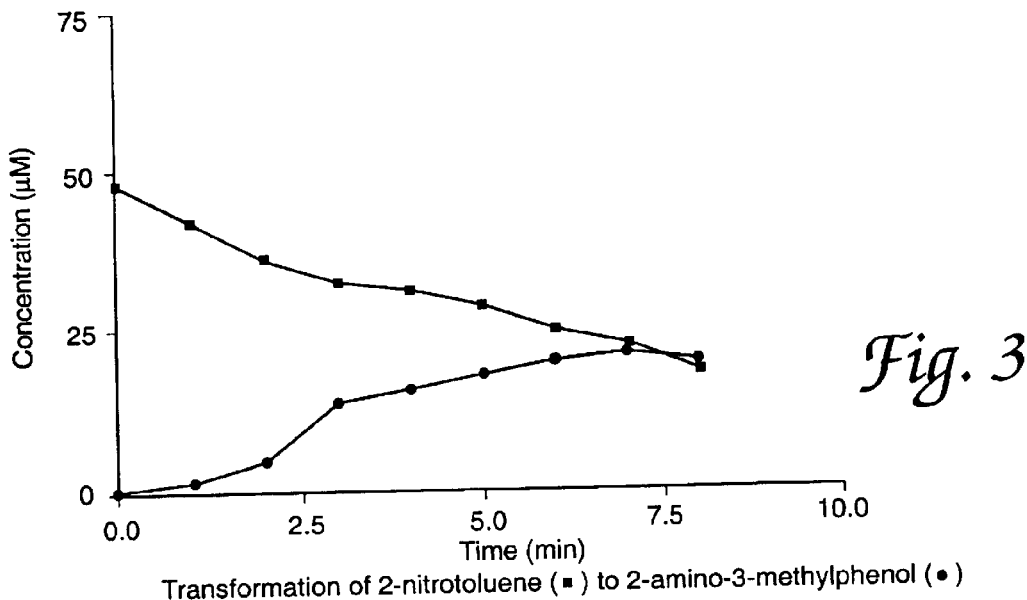
FIG. 3 illustrates the transformation of 2-nitrotoluene to 2-amino-3-methylphenol.
Figure 4:
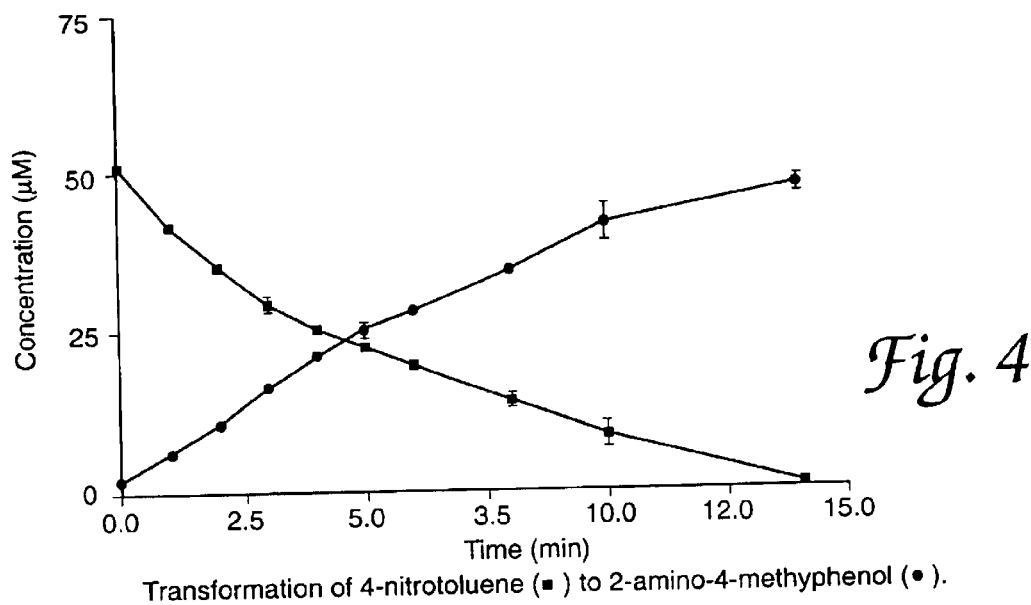
FIG. 4 illustrates the transformation of 4-nitrotoluene to 2-amino-4-methylphenol.
Figure 5:
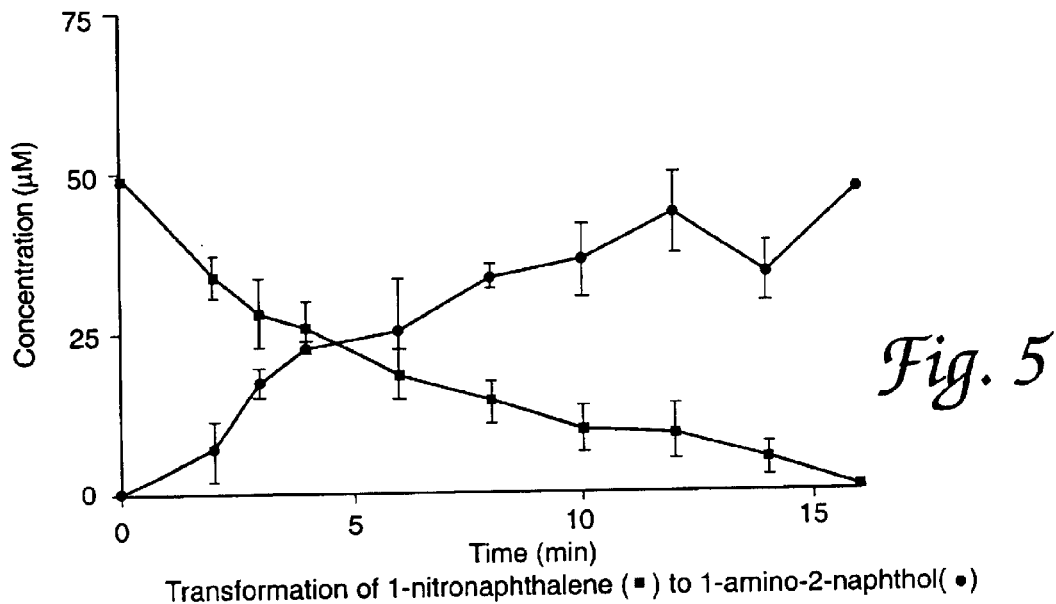
FIG. 5 illustrates the transformation of 1-nitronaphthalene to 1-amino-2-naphthol.
Figure 6:
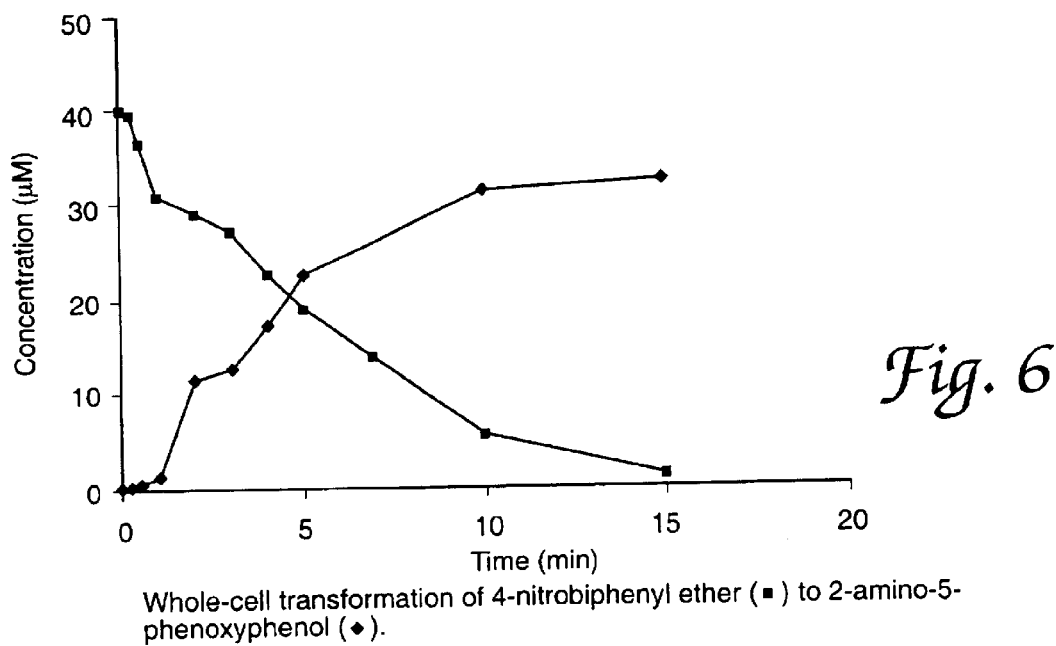
FIG. 6 illustrates the whole-cell transformation of 4-nitrobiphenyl ether to 2-amino-5-phenoxyphenol.

The process of this invention can be carried out as a batch process or as a continuous process. As noted previously, the process uses an enzyme system consisting of pure enzymes, partially purified enzymes, cell lysate, intact cells, or a metal reaction linked with a subsequent enzymatic reaction.

Thus, in one embodiment, the process is a batch or continuous process in which whole cells of non-recombinant or recombinant bacterial strains carrying genes for the synthesis of a nitroreductase enzyme, hereinafter referred to as reductase, and a mutase enzyme, hereinafter referred to as mutase, are used to convert a nitroarene to the corresponding ortho-aminophenol.

In another embodiment, partially purified reductase and mutase are used in a batch or continuous process.

In yet another embodiment, cell lysates of bacterial strains carrying genes for the synthesis of a nitroreductase enzyme and a mutase enzyme are used in a batch or continuous process.

In a further embodiment, nitroreductase and a mutase enzymes expressed from cloned genes are used in a batch or continuous process.

In a yet further embodiment, transformation of the nitroarene to the hydroxylaminoarene is catalyzed by a metal, such as zinc, after which the mutase then catalyzes the transformation of hydroxylaminoarene to the corresponding ortho-aminophenol The following examples illustrate the invention:

Partial Purification of the Enzymes

*Pseudomonas pseudoalcaligenes* strain JS45 was grown and crude cell extracts were prepared as described by Nishino and Spain, Degradation of nitrobenzene by a *Pseudomonas pseudoalcaligenes*, Appl. Environ. Microbiol., 59: 2520–2525 (1993). The nitrobenzene nitroreductase was purified as described by Somerville, Nishino, and Spain, Purification and characterization of nitrobenzene nitroreductase from *Pseudomonas pseudoalcaligenes* JS45, J. Bacteriol., 177: 3837–3842 (1995). The crude extract was loaded on a 100 ml Q-Sepharose Fast Flow column (Pharmacia, XK-26) previously equilibrated with 150 mM KCl in 20 mM phosphate buffer. Proteins were eluted with a step gradient that began with 100 ml buffer containing KCl (150 mM) and then a linear gradient of 150 to 300 mM KCl at a flow rate of 2.5 ml/min. The fractions containing nitrobenzene nitroreductase activity, which eluted in the linear gradient between 65 to 80 ml, were pooled, washed three times and concentrated on an Amicon PM-10 membrane and stored in 500 µl aliquots at −80° C. for use in transformation assays. Partial purification of the Hab B mutase from *E. coli* (pNBZ139) which contains habB was performed as described by He, Nadeau and Spain, Characterization of hydroxylaminobenzene mutase from pNBZ139 derived from *Pseudomonas pseudoalcaligenes* JS45: a highly-associated sodium-dodecyl-sulfate-stable enzyme catalyzes an intramolecular transfer of hydroxyl groups, Eur. J. Bioch., 267: 1110–1116 (2000).

Chemicals

4-Nitrobiphenyl ether, nitrobenzene, 2-nitrotoluene, 4-nitrotoluene, 2-amino-3-ethylphenol, 2-amino-4-methylphenol, n-butylboronic acid and zinc dust were obtained from Sigma-Aldrich (St. Louis, Mo.). 1-Nitronaphalene and 1-amino-2-naphthol were purchased from Fluka (Milwaukee, Wis.) and Pfaltz and Bauer (Waterbury, Conn.), respectively. Bistrimethylsilyltrifluoro-acteamide (BSTFA) was purchased from Aldrich (Deerfield, Ill.). Hydroxylaminobenzene was synthesized according to the method of Fumiss, Hannaford, Smith, and Tatchell, Vogel's Textbook of Practical Organic Chemistry, John Wiley & Sons, New York, 1989.

4-Hydroxylaminobiphenyl ether was synthesized by the method of Miyauchi, Takao, Watanabe, and Uematsu, Mutagenic activity of possible metabolites of 4-nitrobiphenyl ether, Chem-Biol Interact., 51: 49–62 (1984). The melting point was 72.8 to 73.6° C. and the $A_{max}$ was 245.6 nm in ethanol which compared well to the published results of 71.0 to 74.0° C. and 246 nm, respectively.

Analytical Methods

A high performance liquid chromatograph (HPLC) equipped with a diode array detector monitoring $A_{210}$ (Hewlett-Packard, Model 1040M, Wilmington Del.) was used to identify and quantitate the nitroarenes, intermediates and corresponding aminophenols. 4-Nitrobiphenyl ether and products, and nitrobenzene and products were separated by paired-ion chromatography on a $C_8$ Spherisorb column (250 mm×4.6 mm; Alltech, Deerfield, Ill.) with methanol and water, both containing 0.5 mM hexane-sulfonic acid (low UV Pic B-6 reagent, Waters, Milford, Mass.), as the solvent system at a flow rate of 1.2 ml/min. For the whole cell transformation experiments, the nitroarenes and products were separated on an ABZ column (Supelco, Bellefonte, Pa.) using acetonitrile/water as solvent system. Capillary gas chromatography/mass spectral (GC/MS) analyses were performed splitless on a Hewlett-Packard GC (model 5890) equipped with a mass selective detector (model 5971) and a DB-5 column (J & W Scientific, Folsom, Calif., 30 m long×0.25 mm I.D.×1.0 μm film thickness). The aminophenol derivatized with BSTFA was analyzed by GC/MS using the temperature program beginning at 100° C. and increased 10° C./min to 280° C. The n-butylboronic acid derivative was analyzed using an initial temperature of 50° C. increasing 20° C./min to 340°C. Nitrobenzene nitroreductase activity was measured spectrophotometrically by following NADPH oxidation as previously described.

Thin layer chromatography (TLC) purification of the aminophenol was performed on a 1 mm thick silica plate (PK6F, 60A, Whatman, Clinton, N.J.) using a solvent system consisting of a 20:80 mixture of ethyl acetate-hexane under argon. Samples were extracted in ethyl acetate, dried under argon, and stored at −80° C. until analyzed by HPLC and GC/MS.

EXAMPLE 1

Transformation of 4-NitrobiPhenyl Ether to 2-amino-5-phenoxyphenol

Partially purified nitrobenzene nitroreductase transformed nitrobenzene and 4-nitrobiphenyl ether at rates of 7.9 and 8.1 μmol/min/mg protein, respectively. HPLC analysis of the reaction mixtures initially containing 4-nitrobiphenyl (R.T. 15.8 min.) and the nitroreductase yielded a single product whose LC retention time (5.5 min) and uv spectrum were identical to those of the chemically synthesized 4-hydroxylaminobiphenyl ether. The enzymatic conversion was quantitative, 27.3 μM 4-nitrobiphenyl ether was converted to 26 μM 4-hydroxylaminobiphenyl ether.

Biotransformation for measurement of product accumulation was conducted by incubating 4-nitrobiphenyl ether (30 μM) with partially purified reductase (0.57 mg/protein) and mutase (0.27 mg/mlprotein) in one liter of phosphate buffer (20 mM, pH 7.0, sparged with argon for 1 hr) containing NADPH (200 μM). The HabB mutase was partially purified from a recombinant $E.\ coli$ as described. Biotransformation of 4-nitrobiphenyl ether in the presence of partially purified nitrobenzene nitroreductase and mutase led to the transient accumulation of hydroxylaminobiphenyl ether and then the stoichiometric accumulation of a single product, 2-amino-5-phenoxyphenol. This transformation is shown in FIG. 1.

Transformation of 4-nitrobiphenyl ether for end-product purification was performed in 1 liter of phosphate buffer containing NADPH (1 mM), glucose-6-phosphate dehydrogenase (100 units), glucose-6-phosphate (1 mM), 4-nitrobiphenyl ether (360 μM) dissolved in ethanol and delivered over 2 hours (5 ml final ethanol volume), and nitroreductase (0.18 mg protein added every 30 min). The glucose-6-phosphate dehydrogenase and glucose-6-phosphate were used as an NADH regenerating system. After 2 hours the hydroxylaminobenzene mutase (0.261 mg protein) was added to complete the transformation. The reaction mixture was stirred under argon at 22° C. and the progress of the reaction was monitored by HPLC. Subsequent additions of enzyme were made as necessary to complete the transformation. At the end of the incubation the reaction mixture was extracted four times with 500 ml of ethyl acetate (sparged with argon). Extracts were dried over sodium sulfate, concentrated under nitrogen and stored at −80° C. until purified by TLC, as described below. This large-scale transformation and purification by TLC yielded 34.6 mg of red crystals (48% yield). The product had a melting point of 118.5 to 124.9° C. The reported melting point of 2-amino-5-phenoxyphenol is 123.5 to 125.0° C.

The end-product was also purified by HPLC and analyzed by GC/MS which revealed a compound with parent ion at m/z 201 consistent with the expected mass of 201.23. The fragment ions at m/z 172 (M-29), 124 (M-77), 96 (M-105), and 77 (M-124) were consistent with the losses of CHO, $C_6H_5$, $C_7H_5O$ and $C_6H_6NO_2$. Derivatization with BSTFA yielded a mixture of compounds: the major component had a parent ion at m/z 273 consistent with the derivatization of one substituent. The minor component had a parent ion at m/z 345, consistent with the expected mass of the compound containing two trimethylsilane moieties. The derivative contained two trimethylsilane groups indicating that the compound contained two available functional groups that could be derivatized. The derivatization pattern is consistent with that of an aminophenol. The position of the substituents was verified by derivatization with n-butylboronic acid which derivatizes compounds with functional groups in the ortho-position, such as catecholamines or catechols. The expected mass of the derivatized product is 266.8 and the GC/MS analysis revealed a product with a parent ion ($M^+$) at m/z 267 and fragment ions at m/z 253 (M-14), 237 (M-30), 224 (M-43), 211 (M-56), 134 (M-133), and 77 (M-190) corresponding to the possible loss of N or $CH_2$, $C_2H_6$, $C_3H_7$, $C_4H_8$, $C_7H_8NOB$ and $C_{10}H_{13}NO_2B$ which strongly suggests that the end-product is 2-amino-5-phenoxyphenol. The results clearly indicate that the nitroreductase reduces 4-nitrobiphenyl ether to the hydroxylaminobiphenyl and the mutase specifically rearranges 4-hydroxylaminobiphenyl ether to 2-amino-5-phenoxyphenol.

EXAMPLE 2

Cell-lysate Transformation of Various Nitroaromatic Compounds to the Corresponding Ortho-aminophenols The cell lysate of $Pseudomonas\ pseudoalcaligenes$ strain JS45 grown on nitrobenzene was used to catalyze the transformation of a variety of nitroarenes to the corresponding ortho-aminophenols to demonstrate the extensive substrate range of reductase and mutase. The reaction was performed anaerobically in phosphate buffer (1 ml final volume, 20mM, pH 7.0) supplemented with NADPH (500 μM) and the specific nitroarene (50 μM). The reaction was initiated by adding cell lysate (31 μg protein $ml^{-1}$) and terminated by adding samples of the reaction mixture to acetonitrile or methanol and storing on ice. The lysate was centrifuged and concentrations of substrates and products were monitored by HPLC as described below. The transformations of nitrobenzene, 2-nitrotoluene, 4-nitrotoluene and 1-nitronaphthalene to the corresponding aminophenols are shown in FIGS. 2–5, respectively.

EXAMPLE 3

Whole Cell Transformation of 4-Nitrobiphenyl Ether to 2-amino-5-phenoxyphenol $P.\ pseudoalcaligenes$ JS45 was grown as previously described, pelleted by centrifugation at 8000×g for 5 minutes at 4° C., washed once in phosphate buffer (20 mM, pH 7.0), pelleted and suspended in phosphate buffer to approximately $A_{600}$ of 1.2. The reactions, carried out in 3 ml of the cell suspensions in aerobic conditions at 22° C., were initiated by the introduction of 4-nitrobiphenyl ether (approximately 40 μM). The reactions were terminated by addition of an equal volume of reaction mixture to cold, acidified acetonitrile (0.1% trifluoroacetic acid, v/v) and the cells were pelleted by centrifugation at 15,800×g for 1

EXAMPLE 4

Chemical Reaction Coupled to an Enzymatic Reaction to Produce Aminophenols from Nitroarenes The biological, chemical and electrochemical reduction of a nitroaromatic compound to a hydroxylaminoarene occurs by the transfer of four electrons and protons:

$$ArNO_2 + 4e + 4H^+ \rightarrow ArNHOH + H_2O$$

Hydroxylaminoarenes can be chemically synthesized from nitroaromatic compounds by using metals, such as zinc, or by using ammonium sulfate. For example, hydroxylaminobenzene is readily synthesized in an aqueous solution containing ammonium chloride and 2 mol of zinc per mol of nitrobenzene.

The mutase (enzyme) activity was stable in reaction conditions used to reduce nitrobenzene to the hydroxylaminobenzene. A typical reduction reaction mixture contained nitrobenzene (7.3 μmol), ammonium chloride (0.5 mg) and zinc (15 μmol) in 1.5 mL deionized water, and the reaction was kept in suspension by mechanical stirring. At appropriate intervals samples were removed from the reaction mixture. The zinc was removed by centrifugation and the supernatant was monitored for substrate disappearance and product formation by high performance liquid chromatography. The cell lysate (50 μl; 1.9 mg protein) was added after the hydroxylaminobenzene had accumulated in the supernatant. The enzymatic conversion proceeded for 2 minutes. The yield of 2-aminophenol was 47%. In other experiments the enzyme was added at the beginning of the reduction reaction and similar results were obtained.

The chemically synthesized hydroxylaminobenzene is relatively stable making it a model compound for biological studies. It was converted to 2-aminophenol by mutase, HabA, expressed in recombinant bacteria, and by mutase HabB in partially purified extracts. The above experiments demonstrated that the chemical reduction of the nitroarene to the hydroxylaminoarene can be coupled with the enzyme-catalyzed transformation of the hydroxylaminoarene to the ortho-aminophenol.

An enzyme catalyzed process is advantageous over chemical synthesis because the enzymatic process produces ortho-aminophenols in high yield. The biological process does not require the use of the metals and harsh conditions that are typical of the chemical process. Therefore, it reduces the production of wastes.

Having thus described exemplary embodiments of the present invention, it should be noted by those skilled in the art that the disclosures herein are exemplary only and that alternatives, adaptations and modifications may be made within the scope of the present invention.

We claim:

1. A process for the production of an ortho-aminophenol from a nitroarene of the formula

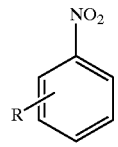

wherein R is selected from the group consisting of —H, —OH, —COOH, —$C_nH_{2n+1}$, —$C_6H_5$, —X, —$CX_3$, —CHO, —$OC_nH_{2n+1}$, and —O—$C_6H_5$, wherein n ranges from 1 to 6, and X is F, Cl, Br or I, which comprises transforming said nitroarene to the corresponding hydroxylaminoarene with a metal catalyst and transforming said hydroxylaminoarene to said ortho-aminophenol using a biocatalyst consisting essentially of a mutase enzyme that converts said hydroxylaminoarene to said ortho-aminophenol, and recovering a fraction containing said ortho-aminophenol.

2. The process of claim 1 wherein said metal is zinc.

* * * * *